United States Patent [19]
Heimer

[11] Patent Number: 5,892,625
[45] Date of Patent: Apr. 6, 1999

[54] FLUID IMAGE TRANSMITTING OPTICAL SYSTEM FOR ENDOSCOPES

[75] Inventor: Richard J. Heimer, Los Angeles, Calif.

[73] Assignee: Radiant Optics, Inc., Los Angeles, Calif.

[21] Appl. No.: 890,583

[22] Filed: Jul. 9, 1997

[51] Int. Cl.$^6$ ............................................. G02B 1/06
[52] U.S. Cl. ............................................. 359/665
[58] Field of Search ........................... 359/434, 665–667

[56] References Cited

U.S. PATENT DOCUMENTS

| | | | |
|---|---|---|---|
| 2,171,640 | 9/1939 | Berek | 88/57 |
| 3,257,902 | 6/1966 | Hopkins | 88/57 |
| 3,364,816 | 1/1968 | Jeffree | 88/24 |
| 3,799,656 | 3/1974 | Fleischman | 350/222 |
| 4,168,882 | 9/1979 | Hopkins | 359/434 |

*Primary Examiner*—Georgia Epps
*Assistant Examiner*—Michael A Lucas
*Attorney, Agent, or Firm*—Rockey, Milnamow & Katz, Ltd.

[57] ABSTRACT

A low cost image transmission optical system for an inflexible type endoscope comprising two rod-like lenses disposed in a front-to-back symmetrical manner, each rod-like lens consisting of two correcting lenses encapsulating therebetween a fluid; said fluid, for example, may be water or an optical liquid. The said encapsulated fluid image transmission optical system being arranged that the image brightness and its chromaticity, curvature of field and astigmatic residuals are favorably corrected, and that the said arrangement is not susceptible to breakage when a bending load is applied to the shaft of the endoscope.

24 Claims, 12 Drawing Sheets

FIG. 12
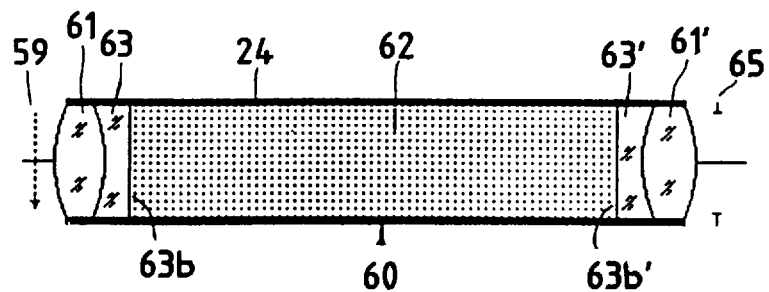
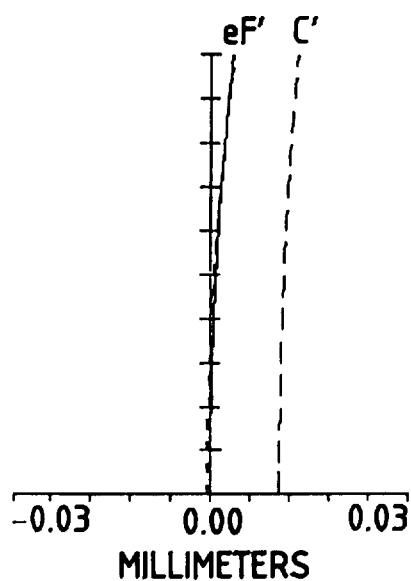
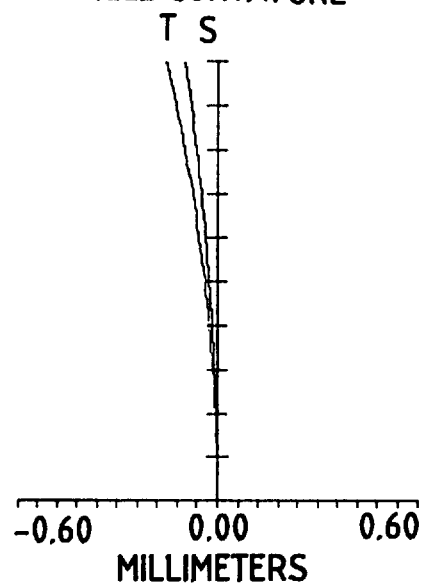
FIG. 13

FLUID IMAGE TRANSMITTING OPTICAL SYSTEM FOR ENDOSCOPES

BACKGROUND OF THE INVENTION

A) Field of the Invention

The present invention relates to a biconvex rod-lens for the optics assemblies of medical or technical endoscopes, and a rod-lens comprising a fluid encapsulated between two correcting lenses, the external surfaces of which are convex in shape and, more particularly, to an inexpensive and durable image transmission optical system to be used with an inflexible-type endoscope or the like, which is arranged to transmit an image by using a plural number of relay lenses.

B) Description of the Prior Art

An inflexible-type endoscope 1 illustrated in FIG. 1 consists of an eyepiece 2 to the distal end of which is affixed a connector 7a for attachment of a fiber optics light delivery assembly (not shown) and a tubular outer shaft 3 receiving the optical elements of the assembly. The said optical elements, shown in FIG. 1A, consist of the objective 8 which is arranged near the distal end of shaft 3, and a series of lenses 9 arranged to transmit an image from the proximal end of objective 8 to the distal portion of eyepiece 2.

According to the prior art, as illustrated in FIG. 2, an image transmission optical system consists of two rod-like cemented doublets 9, each consisting of the biconvex positive lens element 12 made, for example, from a crown glass and the concavo-convex negative lens element 14 cemented to lens 12, and being made, for example, from a flint glass. Said image transmitting optical system is arranged so that the convex surfaces of the negative lens elements 14 thereof face each other in opposition, said assemblies embraced in a thin-walled inner tube 10 within the outer shaft 3 in an eccentric and interlocking relationship. The said rod-like cemented doublets 9 are held in longitudinally spaced relationship by means of thin-walled tubular spacers 11. The shaft 3 and inner tube 10 cooperate to define a space which has a crescent-shaped cross section and in which are arranged fiber optics light guides 7 for transmitting light fed through connector 7a, to the distal end of endoscope assembly 1.

The rod-like lens 9, an enlarged view of which is shown as FIG. 3, is hereinbefore described as a cemented doublet purely on the basis that such nomenclature is a suitable matrix for optical design purposes. The positive lens 12 of a cemented doublet 9, however, is not amenable to low cost, volume manufacturing. Accordingly, it has become customary and prudent to divide positive lens 12 of rod-like lens 9 into three parts, to wit, plano-convex lens 12a, plano-plano lens 12b, and plano-convex lens 12c, so that said lenses can be economically and simultaneously processed as individual parts in multiples.

Once fabricated, the individual lenses are subsequently joined as a cemented assemblage comprising lens 12a, lens 12b, and lens 12c which is equivalent in form and function to monolithic rod lens 12. Said lens assembly, as shown in FIG. 4, is cemented to negative lens 14 to form a quadruplet lens assembly 13 which is equivalent in form and function to doublet 9. It should also be mentioned in passing that the fractionation process of rod-like lens 12 has its limits. Typically, there is economic justification for dividing the rod-like lens 12 into three or fewer pieces; however, should the rod-like lens 12 be required to be processed in four or more pieces, the cost of assembly outweighs the potential savings afforded by fabricating the lenses in multiples.

In its clinical application, the endoscope 1 is inserted into a human subject by grasping it by its proximal end, manipulating its distal end of shaft 3 through a natural or incised aperture, into the interior of a viscera. Such procedure may inadvertently cause the outer tube 3 to be deformed or bent at its approximate mid-length, the extent of which depending on the anatomy of the viscera, the force applied and the modulus of elasticity of the outer tube 3. As a concomitant result of the bending of outer tube 3, inner tube 10 is subjected to not only bending forces but also to compressive forces. Due to the small diameter and considerable length of the rod-like lens 9 and given that it is in a close tolerance embrace with inner tube 10, said lenses are prone to fracture when inner tube 10 is otherwise compressed and bent, especially at the cemented joints.

There is known an image transmitting optical system having a composition as illustrated in FIG. 5. Said known image transmitting optical system is composed of rod-like lens assembly 13, in which the mechanical diameter at the middle of the rod lens is less than the outer diameter at its ends, thus providing clearance between the mid-portion of the rod-like lens and inner tube 10. Rod lenses so shaped are supported in the inner tube 10 merely at their end regions, so that the lens assembly 13 is purported to be protected from fracture or breakage at the cemented joints when the inner tube 10 is bent.

There is known another image transmitting optical system having a composition as illustrated in FIG. 6. Said image transmitting optical system is composed of rod-like lens assembly 13, in which there is present at least one cylindrical collar of greater diameter than the adjacent lengths of each of the rods. Rod lenses so shaped are supported in their inner tube 10 only by way of the said collars, thus providing clearance between the rod-like lens and the inner tube 10 at the regions adjacent to the cylindrical collars and therefore purporting to protect the cemented joint from stress and possible fracture when the inner tube 10 is bent.

The aforementioned known methods of eliminating the possibilities for stress fractures of the rod lenses in image transmitting optical systems have, nevertheless, several significant drawbacks.

First and foremost, there remains, despite the aforementioned precautions, the distinct possibility that the cemented joints located at either ends of the rod-like lenses may be subjected to shear stress sufficient for risk of fracture. This is simply the result of the aforementioned mounting constraints existing at one end portion or both end portions of the rod-like lens assembly where one or more cemented joints may be located. Second, the economy of manufacture is impacted by the additional requirements of edging and centering the rod-like lens assembly which does not exhibit a uniform diameter along its length. Third, by constraining the diameter of the rod-like lenses of the image transmitting optical system for the purpose of eliminating stress fractures when the inner tube 10 is bent, an unnecessarily restrictive aperture stop and/or field stop my be created which places an upper limit upon the maximum value to which the image diameter, numerical aperture, or both, may reach. Consequently, this may have an unfavorable effect upon the luminous energy throughput or étendue of the image transmitting optical system.

Thus, a need has arisen for an image transmitting optical system which is inexpensive, durable and energetically efficient relative to known image transmitting optical systems. This need is pronounced when it is desired to utilize the said image transmitting optical system in an inflexible-type endoscope.

SUMMARY OF THE INVENTION

It is the object of this invention to provide a rod lens constructed for the avoidance of shear stresses in the rod-like lenses when the inner tube of the endoscope is inevitably bent. It is another object of the invention to provide an improved image transmitting optical system having elements which are substantially less expensive to manufacture than the elements of conventional systems. A further object is to provide an improved image transmitting optical system having optical performance characteristics that are substantially superior to the performance characteristics of conventional prior art systems.

The above and other objects of the invention will become more readily apparent when the following description is read in conjunction with the accompanying drawings.

BRIEF DESCRIPTION OF THE DRAWINGS

FIG. 12 is a sectional view of a rod lens according to Embodiments 11 of the present invention;

FIG. 13 through FIG. 23 respectively show graphs of the longitudinal aberration and the astigmatic field curves of Embodiments 1 through 11 of the present invention.

DESCRIPTION OF THE PREFERRED EMBODIMENTS

Figure 2:
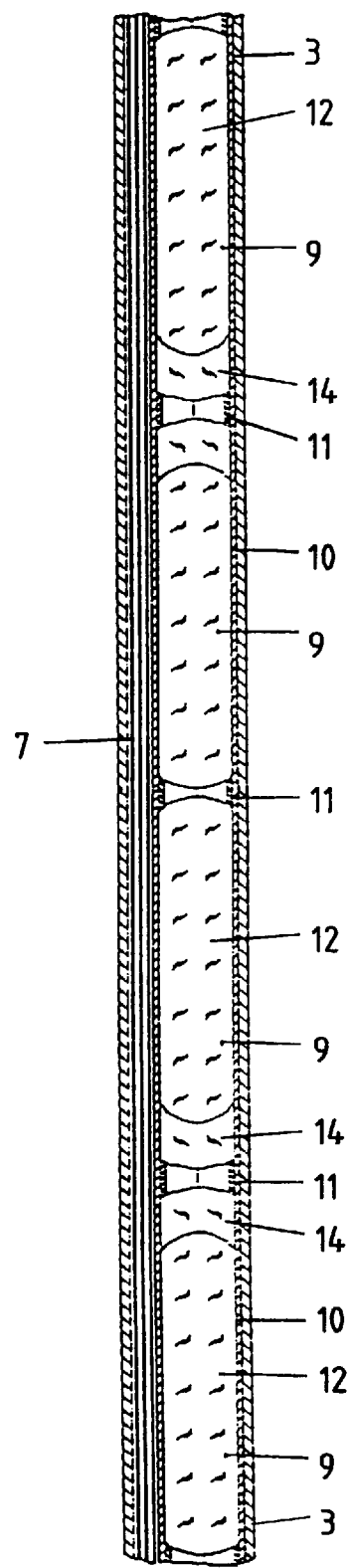
FIG. 2 is a longitudinal sectional view through part of the distal portion of the assembly, as indicated by the chain oval II in FIG. 1.
Figure 3:
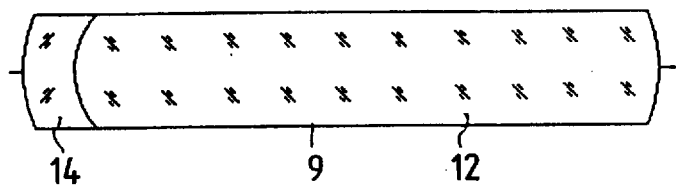
FIG. 3 is a sectional view of a conventional rod lens for the assembly with the rod lens comprising a rod having a negative correcting lens cemented thereto, as is the customary depiction for the purpose of calculating the optical design.
Figure 4:
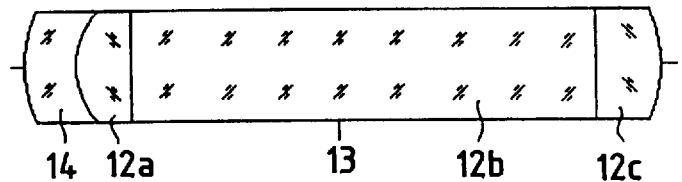
FIG. 4 is a sectional view of a conventional rod lens for the assembly with the rod lens, comprised of three parts cemented together, and a negative correcting lens cemented thereto, as the rod lens is actually fabricated.
Figure 5:
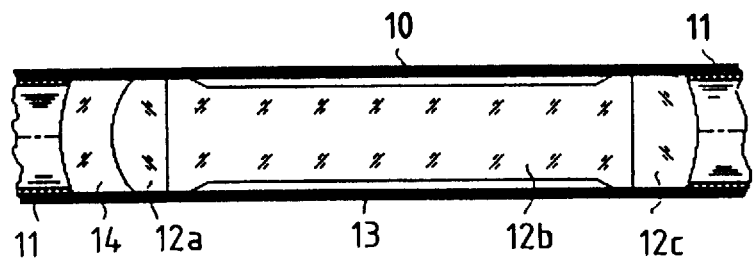
FIG. 5 is a sectional view of the prior art lens of FIG. 4 after reduction in the diameter of the rod lens in the middle region of said rod.
Figure 6:
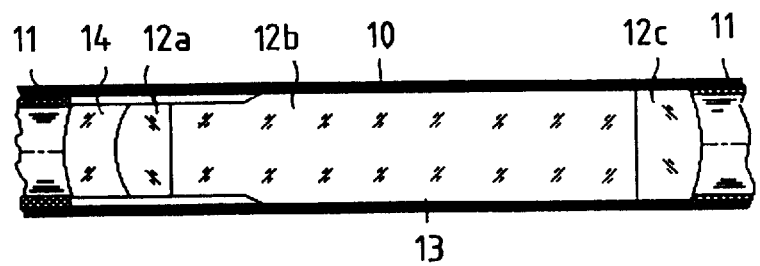
FIG. 6 is a section view of the prior art lens of FIG. 4 after reduction in the diameter of the rod lens in the region of the negative correction lens.

Prior to describing details of the present invention, the general method of designing an optical system, particularly an image transmitting optical system exemplified in FIG. 2, will be discussed. Much of modern lens design consists of the selection of a starting lens form and its subsequent optimization by a computer-aided lens design program, the function of which is to drive the design form to its nearest local optimum as defined by a defect function. The defect function is intended to completely describe, with a single number, the value or quality of a given lens design. A typical defect function, for example, is the sum of the squares of many image defects. The defects may be of many different kinds; usually, most are related to the quality of the image as generated by Seidel aberration coefficients and by exact ray tracing. However, any characteristic which can be calculated may be assigned a target value and its departure from that target regarded as a defect.

The potential variables for use in optimization include: the surface curvatures, conic constants, aspheric deformation coefficients, the spacings between surfaces, and the optical characteristics of the refractive materials involved. The task of the lens design computer program, with lens designer intervention, is to find a location in solution space which minimizes that defect function. The mathematics of this process is described in Spencer's, "A Flexible Automatic Lens Correction Program," *Applied Optics*, Vol. 2, 1963, pp 1257–1264.

The prior art image transmitting optical systems, as hereinbefore described, are portions between successive image planes and are composed of pairs of cemented quadruplet assemblies disposed in a front to back symmetrical arrangement, and operating at unit magnification. The principle of symmetry is invaluable in image transmitting optical systems in that three of the seven Seidel (primary) aberrations, namely, coma, distortion and primary lateral color, are identically zero. The remaining four aberrations, spherical aberration, primary axial color, Petzval curvature and astigmatism, and the primary characteristics of track (object-image distance) and exit pupil distance, are corrected to values which have been selected as acceptable using the available degrees of freedom of the cemented assemblies.

The said image transmitting optical systems, which for purposes of this discussion of optical design, are composed of pairs of symmetrically disposed cemented doublet assemblies wherein a negative lens made of a flint glass is bonded to a positive lens made of a crown glass; the fractionation of this element for fabrication purposes utilizes the same glass type as in its monolithic form.

To design this doublet, there are several steps required using a typical lens design program: define the optical parameters such as aperture, field of view and spectral range of correction; define a starting configuration consisting of surface radii, axial thickness and a suitable pair of glass materials; define the boundary constraints such as minimum edge thickness, focal length, track and exit pupil distance; define the relative importance assigned by the lens designer to image defects and characteristics; define the variables or degrees of freedom to be used in the optimization; and define an optimization goal.

The degrees of freedom in a doublet are two powers, a bending, two lens thicknesses and glass choice. Thus, there are just the necessary six degrees of freedom to address the six primary corrections hereinbefore described. Among the said degree of freedoms, glass choice is the most important design variable, for it is the differences in refractive index and Abbe number, respectively, that provide correction for Petzval curvature and primary axial color aberration.

Figure 7:
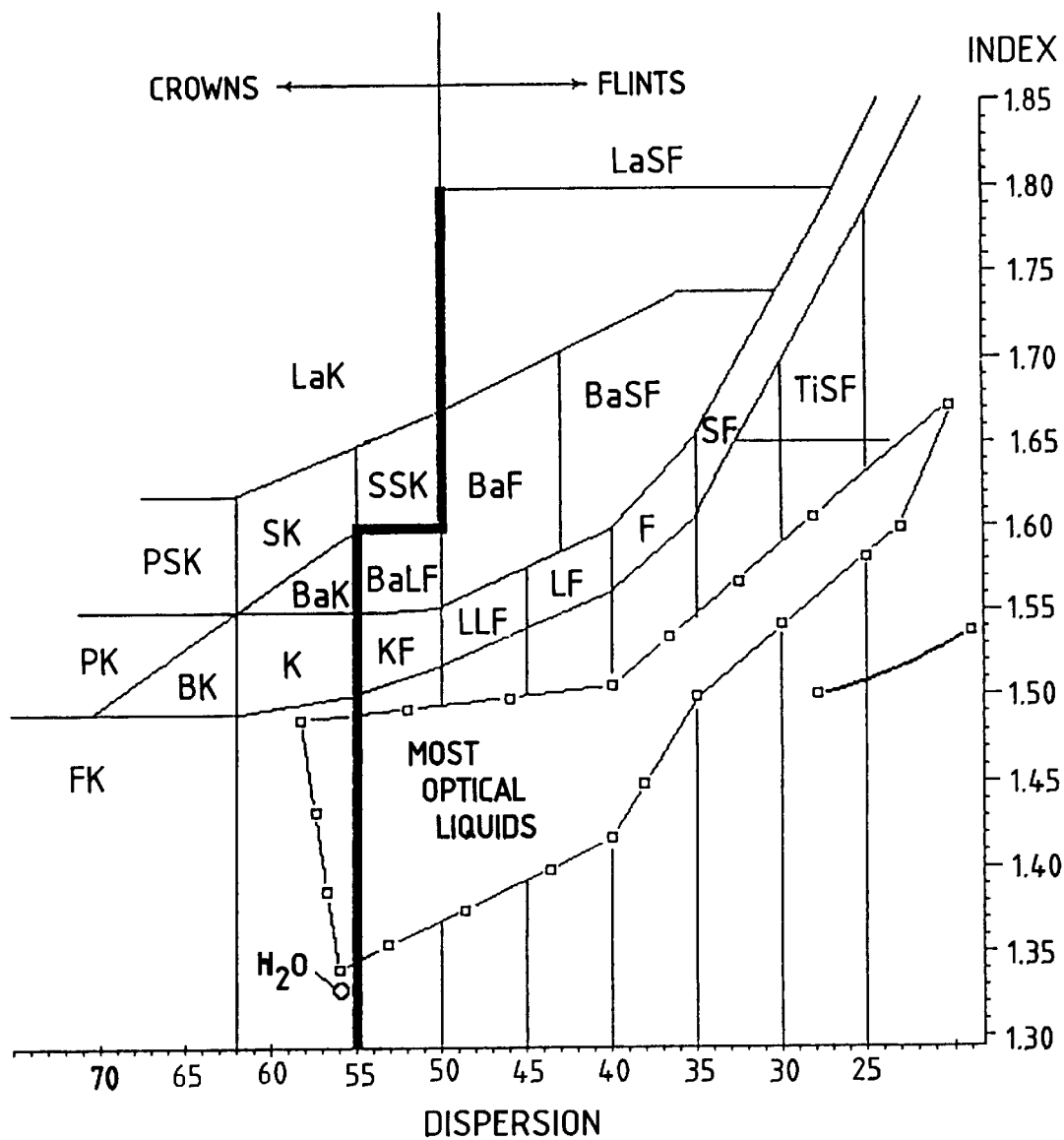
FIG. 7 is a refractive materials veil which plots refractive index, $n_d$, against Abbe value $v_d$, where $v_d=(n_d-1)/(n_F-n_c)$.

There are hundreds of available optical glasses a designer may choose for use in visible light transmitting systems. These glasses are arranged by glass type and are conveniently organized in the form of a glass map, or veil. FIG. 7 is a diagram of optical materials wherein the refractive index, $n_d$, is plotted against the Abbe number, $v_d$, where $$v_d = (n_d - 1)(n_F - n_c)^{-1}$$

and $(n_F - n_c)$ is the principal dispersion. The subscripts d, F and c refer to Fraunhover lines (individual wavelengths) of the visible spectrum.

Optical glasses, such as those manufactured by Schott Glass Technologies, Inc., Duryea, Pa., occupy the upper portion of FIG. 7. The diagram subdivides the various types of glass into groups. The designation given for each type of glass consists of the group designation in abbreviated form and a number, for example, F1 or LaK 8. It has become the custom to designate types of glasses with $n_d > 1.60$, $v_d > 50$, or $n_d < 1.60$, $v_d > 55$ as "crowns," and the others as "flints." A glass "line" is formed and composed of the glasses of types K, KF, LLF, F and SF which are strung along the middle to upper right-hand portion of the diagram bounding glasses to the region of greater Abbe numbers.

If the image transmitting optical system is to be optimized by a suitable defect function for an endoscope, the glass characteristics must be varied. Although the material characteristics are not continuously variable, the index of refraction $n_d$ and dispersion $v_d$ can be varied within the boundaries of the glass map. In the process of optimizing the primary aberrations and characteristics by material parameters, the crown glasses tend to go to the upper left hand corner of the glass map. Flint glasses tend to migrate to the lower right hand corner and are then, of course, constrained to move along the glass "line," limiting the differences in index and Abbe numbers, and thusly, the optimization.

Optical liquids, such as those manufactured by R. P. Cargille Laboratories, Inc., Cedar Grove, N.J., are well known to exhibit a wide range of $n_d$ values and possess generally higher dispersions (lower $v_d$ values). When optical liquid data is imported into the $n_d/v_d$ diagram shown as FIG. 7, it is seen that liquids occupy the lower right corner of the diagram in a region devoid of optical glasses. Expanding the boundaries of the materials map to include optical liquids permits the material refractive characteristics to be freely varied without the previously imposed constraint of the glass "line."

Moreover, optical liquids are known to possess anomalous relative partial dispersions which are greater than those of the few optical glasses similarly disposed. This optical property of liquids can be effectively utilized in the correction of secondary spectrum (the achromatization of more than two wavelengths), an aberration which can seriously affect the image quality of relay optical systems. The possibility thus exists for innovative lens design solutions having index and Abbe number differences which were heretofore not possible with optical glass types alone and it is these solutions that constitute the preferred embodiments.

The preferred embodiments utilize optical liquids as replacement media for the elongated element 12 of the rod-like lens of the image transmitting optical systems. Accordingly, the rod-like lenses of the preferred embodiments, by virtue of a flexible middle portion, are not susceptible to breakage when the shaft of the endoscope is bent. Further, the cost factors associated with material, fabrication and assembly are significantly less than those associated with the conventional image transmitting optical systems.

The illustrative embodiments to be described below include one example each of eleven embodiments of an image transmitting optical system as used in an inflexible type endoscope or the like. The description of the image transmitting optical system of the present invention will be given in terms of a module comprising one-half of the symmetrical pair of rod-like lenses between successive image planes. It will be appreciated that two modules are arranged to form a symmetrically front-to-back oriented pair, rendering an image transmitting optical system.

Figure 8:
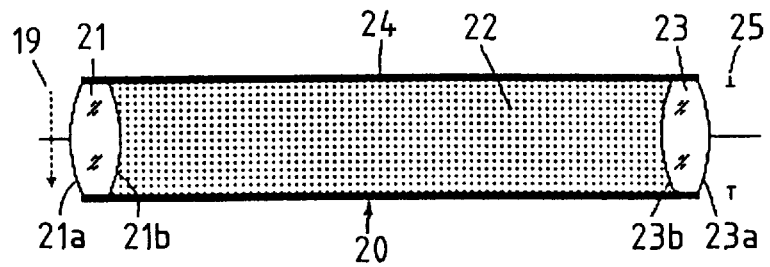
FIG. 8 is a sectional view of a rod lens according to Embodiments 1, 2, 3 and 4 of the present invention.

FIG. 8 is an optical schematic representative of Embodiments 1, 2, 3, and 4. It is seen that the module constitutes an axially aligned triplet assembly 20. Triplet 20 includes first and second lens elements 21 and 23 separated by an optical liquid 22 which is encapsulated between lens elements 21 and 23, and a thin-walled sleeve 24 made of, for example, a fluoropolymer resin such as that manufactured by Zeus Industrial Products, Inc., Orangeburg, S.C. Lens elements 21 and 23 are attached at their cylindrical edge portions by a fastening means to sleeve 24 using, for example, a bonding agent or an adhesive, to form a liquid-tight seal.

The configuration of the module is defined by object plane 19, an anterior convex surface 21a, a liquid contacting surface 21b, a second liquid contacting surface 23b, a posterior convex surface 23a and a pupil plane 25. An aperture stop is provided at surface 25 to define the aperture diameter of the assembly. A field stop at surface 19 is also provided to define the field diameter. The longitudinal positioning of triplet 20 to its symmetrically disposed module is conveniently provided by tubular spacers (not shown).

In Embodiment 1, the biconvex lens 21 is made of a light flint material (LF) of moderately low refraction and dispersion. Biconvex lens 23 is made of a barium crown material (SK) of moderately high refractive index and moderate dispersion. The biconcave lens 20, so formed between lens 21 and 23 and thin-walled sleeve 24, is made of a non-toxic, non-viscous, highly dispersive optical liquid having a refractive index which closely matches that of biconvex lens 21. The large v-value difference across surface 21b provides for the correction of primary axial color without significantly influencing spherical aberration and astigmatism, whereas the difference in refractive indices across surface 23b is used to favorably correct curvature of field. Spherical aberration is corrected by an aspherical surface 23a located in close proximity to aperture stop 25.

The said aspherical surface, specifically a conic section called a prolate spheroid, is preferably fabricated economically as a precision molding, by a compression molding technique and a special moldable optical glass perfected, for example, by Corning Incorporated, Corning, N.Y. The thickness and refractive index of biconcave lens 22, in cooperation with surface 21a, corrects the track and exit pupil distance to target values. The air space thickness preceding aperture stop 25 favorably corrects astigmatism.

It will be appreciated that the image transmission optical system preferred as Embodiment 1 is composed of two modules each having only two biconvex lens elements and an optical liquid therebetween. This simplification of construction translates as reduced cost of manufacturing and assembly, and improved durability.

Embodiments 2 and 3 have compositions each of which is essentially similar to that of Embodiment 1. In contrast to Embodiment 1 in which one of the lens surfaces nearest the aperture stop is a conic surface, each of the surfaces of are designed as spherical surfaces. Further, Embodiments 2 and 3 exemplify the adaptability of the present invention to various combinations of optical glass types for transmitting an image and correcting the aberrations of the same.

In Embodiment 4, the biconvex lenses 21 and 23 are made of polymethyl methacrylate (acrylic), often referred to as the "crown" of plastics. The biconcave lens 20, so formed between lens 21 and 23 and the thin-walled sleeve is made of a non-toxic, non-viscous, dispersive optical liquid having disparate refractive indices compared to those of acrylic. The resultant large differences in $n_d$ and $v_d$ across liquid contacting surfaces 21b and 23b provide for the favorable correction of curvature of field and primary axial color.

Spherical aberration is corrected by an aspheric surface 23a located in close proximity to aperture stop 25. An aspheric surface 21a corrects spherical aberration of the exit pupil. The said aspheric surfaces 21a and 23a, the exterior surfaces of acrylic lenses 21 and 23 respectively, are conic sections, specifically prolate spheroids, which are preferably fabricated by a precision injection molding technique perfected, for example, by Opkor, Inc., Rochester, N.Y.

The thickness of biconcave lens 22 corrects the track and exit pupil distance to target values. The airspace thickness preceding aperture stop 25 favorably corrects astigmatism. It will be appreciated that the image transmission optical system preferred as Embodiment 4 is composed of two modules each having only two substantially similar biconvex acrylic lens elements and an optical liquid, a composition affording low cost and durability.

Now, the numerical data for Embodiments 1, 2, 3, and 4 of the present invention will be given below. The following nomenclature will be adopted. The radius of a given surface i will be designated as $R_i$, the distance between a given pair of adjacent surfaces i and j will be designated $t_{ij}$, the index of refraction and Abbe number of the material medium between given surfaces i and j will be designated $n_{ij}$ and $v_{ij}$, respectively. All dimensions are in millimeters. The aspherical surfaces of Embodiments 1 and 4 are defined by the expression:

$$Z_i = c_i r_i^2 \{1+[1-(k+1)c_i^2 r_i^2]^{1/2}\}^{-1} + d_i r_i^4 + e_i r_i^6 + f_i r_i^8 + g_i r_i^{10}$$

where $Z_i$ is surface sagitta, $c_i$ is the reciprocal radius of curvature, $r_i$ is the radial coordinate of the ith surface, $k_i$ is the conic constant, and $d_i$, $e_i$, $f_i$, and $g_i$ are aspheric coefficients.

Embodiment 1
$NA_0=0.0625$ Object Diameter=2.12 ½ Track=31.80
OBJECT
$T_{0,1}=0.013$ AIR
$R_1=11.731$
$T_{1,2}=1.038$ $N_{1,2}=1.58175$ $v_{1,2}=41.32$
$R_2=-10.735$
$T_{2,3}=28.471$ $N_{2,3}=1.58291$ $v_{2,3}=28.81$
$R_3=21.684$
$T_{3,4}=0.957$ $N_{3,4}=1.60786$ $v_{3,4}=50.11$
$R_4=-12.350$ $k_4=-0.494443$
$T_{4,5}=0.717$ AIR
APERTURE STOP Embodiment 2
$NA_0=0.065$ Object Diameter=2.12 ½ Track=31.80
OBJECT
$T_{0,1}=3.640$ AIR
$R_1=26.250$
$T_{1,2}=1.252$ $N_{1,2}=1.72055$ $v_{1,2}=47.71$
$R_2=-5.298$
$T_{2,3}=24.643$ $N_{2,3}=1.56685$ $v_{2,3}=19.43$
$R_3=61.935$
$T_{3,4}=1.252$ $N_{2,3}=1.68637$ $v_{2,3}=44.24$
$R_4$–15.730
$T_{4,5}=1.014$ AIR
APERTURE STOP Embodiment 3
$NA_0=0.065$ Object Distance=2.12 ½ Track 31.80
OBJECT
$T_{0,1}=4.031$ AIR
$R_1=26.250$
$T_{1,2}=1.252$ $N_{1,2}=1.79226$ $v_{1,2}=47.24$
$R_2=-7.988$
$T_{2,3}=25.165$ $N_{2,3}=1.56685$ $v_{2,3}=19.43$
$R_3=66.245$
$T_{3,4}=1.252$ $N_{3,4}=1.79226$ $v_{3,4}=47.24$
$R_4=-19.649$ $K_4=0.081389$
$T_{4,5}=0.100$ AIR
APERTURE STOP Embodiment 4
$NA_0=0.058$ Object Diameter=1.94 ½ Track=31.80
OBJECT
$T_{0,1}=0.009$ AIR
$R_1=9.446$ $K_1=-0.45048$
$T_{1,2}=0.983$ $N_{1,2}=1.4938$ $v_{1,2}=57.75$
$R_2=-32.398$
$T_{2,3}=29.742$ $N_{2,3}=1.5827$ $v_{2,3}=30.14$
$R_3=32.398$
$T_{3,4}=0.983$ $N_{3,4}=1.4938$ $v_{3,4}=57.75$
$R_4=-9.446$ $K_4=-0.45048$
$T_{4,5}=0.084$ AIR
APERTURE STOP FIG. 13 through FIG. 16 illustrate the aberration characteristics of Embodiments 1, 2, 3 and 4 when each is arranged in symmetrical opposing pairs of modules about their respective aperture stops. The characteristics shown are longitudinal aberration and astigmatic field curves plots as a function, respectively, of relative normalized pupil radius and relative normalized image height, the former shown at three wavelengths, i.e., e (546.1-nm), C' (643.8-nm) and F' (480-nm).

Figure 9:
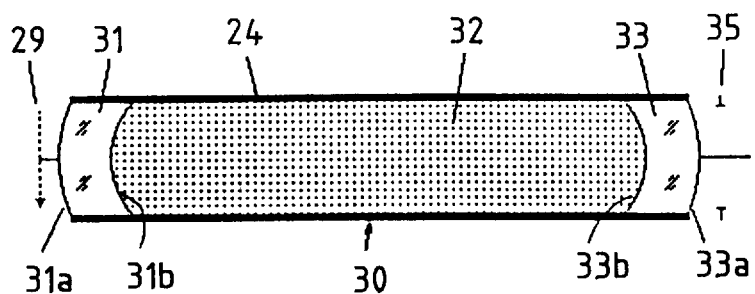
FIG. 9 is a sectional view of a rod lens according to Embodiments 5, 6, 7 and 8 of the present invention.

Whereas Embodiments 1, 2, 3, and 4 are arranged in a power distribution +−+, Embodiments 5, 6, 7, and 8 permutate this distribution as −+−as illustrated in the optical schematic of FIG. 9. It is seen that the module comprises an axially aligned triplet assembly 30. Triplet 30 includes first and second lens element 31 and 33 separated by a non-toxic, non-viscous optical liquid 32 which is encapsulated between lens elements 31 and 33 and a thin-walled sleeve 24. Lens elements 31 and 33 are fastened to sleeve 24, as hereinbefore described, to form a liquid-tight seal.

The configuration of triplet 30 is defined by an object plane 29, an anterior convex surface 31a, a concave liquid contacting surface 31b, a second concave liquid contacting surface 33b, a posterior convex surface 33a, and a pupil plane 35. An aperture stop is provided at surface 35 is provided to define the aperture of the assembly. A field stop is also provided at surface 29 to define the field diameter. The proper spacing of triplet 30 to its symmetrical disposed module, as previously described, is conveniently provided by tubular spacers (not shown).

In Embodiment 5, the convex-concave lenses 31 and 33 are made of a barium flint (BaF) of high index of refraction and moderate dispersion. The biconvex lens 32, so formed between lenses 31 and 33, and the thin-walled spacer 24, is made of an optical liquid having a low refractive index and a low dispersion. A large index and v-value difference across surfaces 31b and 33b provide for the favorable correction of primary axial color and curvature of field. Spherical aberration is corrected by the bending of lenses 31 and 33. The thickness and refractive index of lens 32, in cooperation with surface 33a, favorably corrects the track and exit pupil distance.

Embodiments 6, 7, and 8 have configurational compositions each of which are similar to Embodiment 5. In contrast to Embodiment 5, however, Embodiments 6, 7, and 8 utilize, in the flexible middle portion of the rod-like lens, i.e., the biconvex liquid lens 32, sterile water as the refractive medium. Whereas Embodiment 5 utilizes refractive surfaces which are all spherical in shape, Embodiments 6, 7, and 8 utilize an aspherical surface for the correction of spherical aberration.

In Embodiment 6, the convex-concave lens elements 31 and 33 make use of dense flint glass (SF) of high refractive index and high dispersion (low v-value). As illustrated in FIG. 7, water has "crown-like" optical properties, i.e., $n_d<1.60$, $n_d>55$. Inasmuch as the refractive index of water is low, the refractive index and Abbe number differences across liquid contacting surfaces 31b and 33b are favorable for the correction of the primary axial color and curvature of field. An aspherical surface 33a, specifically a conic section known as an oblate spheroid, in close proximity of the aperture stop surface 35, corrects spherical aberration. The thickness of biconvex liquid lens 32 and the air space between surface 33a and aperture stop correct astigmatism, track and exit pupil distance.

In Embodiment 7, the convex-concave lens elements 31 and 33 make use, respectively, of optical glasses which are a zinc crown (ZK) and a dense flint (SF) type. The refractive index difference across the liquid contacting surface 31b is useful for correction of curvature of field without affecting primary color, since there is a minimal difference in Abbe number at this interface. The refractive index and v-value differences across the liquid contacting surface 33b provides for correction of primary axial color and astigmatism. An aspherical surface 33a, specifically a conic section known as an oblate spheroid, in close proximity of the aperture stop surface 35, favorably corrects spherical aberration. The length of fluid lens 32 is utilized to correct the design for track and exit pupil distance.

In Embodiment 8, the convex-concave lens elements 31 and 33 make use of polystyrene (styrene), the "flint" of optical plastics with excellent molding properties. When combined with the liquid (water) lens 32, the refractive index and Abbe number differences across liquid contacting surfaces 31b and 33b provide means for the correction of primary axial color and curvature of field. As previously described, surface 33a is a conic surface, a prolate spheroid, utilized to correct spherical aberration. Lenses 31 and 33 are preferably fabricated by a precision injection molding process. The center thickness of liquid lens 32 and the center thickness preceding the aperture stop is used to correct the track and exit pupil distance, and astigmatism, respectively.

Embodiment 8 affords an exceptionally low cost alternative to rod-like glass lenses of the image transmitting optical systems in that the lenses 31 and 33 can be duplicated in plastic, holding even tighter focal-length tolerances than conventional glass fabrication, and for less than half the cost of a glass counterpart. Coupled with lens 32, comprising surfaces 31b and 33b and thin-walled sleeve 24, the water filled capsule thusly formed would be an exceedingly cost effective assembly compared to the prior art.

Now the numerical data for the Embodiments 5, 6, 7, and 8 of the present invention will be given. The nomenclature and surface description hereinbefore described will be adopted.

Embodiment 5
$NA_0=0.058$ Object Diameter=1.94 ½ Track=31.80
OBJECT
$T_{0,1}=5.015$ AIR
$R_1=5.203$
$T_{1,2}=1.000$ $N_{1,2}=1.67341$ $v_{1,2}=46.83$
$R_2=3.172$
$T_{2,3}=24.735$ $N_{2,3}=1.40145$ $v_{2,3}=68.39$
$R_3=-4.915$
$T_{3,4}=1.000$ $N_{3,4}=1.67403$ $v_{3,4}=38.92$
$R_4=-7.606$
$T_{4,5}=0.050$ AIR
APERTURE STOP Embodiment 6
$NA_0=0.058$ Object Diameter=1.94 ½ Track=31.80
OBJECT
$T_{0,1}=6.266$ AIR
$R_1=4.402$
$T_{1,2}=1.000$ $N_{1,2}=1.65222$ $v_{1,2}=33.61$
$R_2=2.970$
$T_{2,3}=23.484$ $N_{2,3}=1.33447$ $v_{2,3}=56.00$
$R_3=-3.970$
$T_{3,4}=1.000$ $N_{3,4}=1.72310$ $v_{3,4}=29.30$
$R_4=-5.723$ $k_4=0.081389$
$T_{4,5}=0.100$ AIR
APERTURE STOP Embodiment 7
$NA_0=0.060$ Object Diameter=1.94 ½ Track 31.80
OBJECT
$T_{0,1}=6.119$ AIR
$R_1=4.858$
$T_{1,2}=1.000$ $N_{1,2}=1.53534$ $v_{1,2}=57.71$
$R_2=2.993$
$T_{2,3}=19.554$ $N_{2,3}=1.33447$ $v_{2,3}=56.00$
$R_3=-3.721$
$T_{3,4}=1.000$ $N_{3,4}=1.85503$ $v_{3,4}=23.65$
$R_4=-5.127$ $k_4=0.023058$
$T_{4,5}=4.130$ AIR
APERTURE STOP Embodiment 8
$NA_0=0.525$ Object Diameter=1.94 ½ Track=31.80
OBJECT
$T_{0,1}=1.127$ AIR
$R_1=4.428$
$T_{1,2}=1.000$ $N_{1,2}=1.59501$ $v_{1,2}=30.62$
$R_2=2.870$
$T_{2,3}=28.573$ $N_{2,3}=1.33447$ $v_{2,3}=56.00$
$R_3=-3.575$
$T_{3,4}=1.000$ $N_{3,4}=1.59501$ $v_{3,4}=30.64$
$R_4=-5.490$ $k_4=0.114157$
$T_{4,5}=0.100$ AIR
APERTURE STOP The aberration characteristics of Embodiments 5, 6, 7 and 8 when each is arranged in symmetrically opposing pairs of modules about their respective aperture stop planes are shown in FIG. 17 through FIG. 20.

Now, in Embodiments 1, 2, 3, and 4, as illustrated in the diagrammatic axial section FIG. 8, it is seen that the fluid lens 22 is substantially biconcave in shape and is of negative optical power. Conversely, in Embodiments 5, 6, 7, and 8, as illustrated in FIG. 9 as a diagrammatic axial section, it is seen that the fluid lens 32 is substantially biconvex and is of positive optical power.

Figure 10:
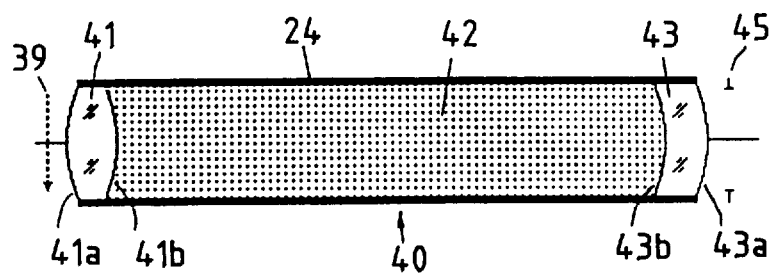
FIG. 10 is a sectional view of a rod lens according to Embodiments 9 of the present invention.

Embodiment 9 of the present invention, shown in the diagrammatic axial section of FIG. 10, is a cross product of the configurations associated with Embodiments 1 through 4 and Embodiments 5 through 8. Embodiment 9 comprises a fluid lens 42 which is concavo-convex in shape and is of positive optical power. Embodiment 9 of the present invention is a module comprising an axially aligned triplet lens assembly 40. Triplet 40 includes a positive power field lens and a negative power meniscus (concavo-convex) lens, said lenses separated by an optical fluid 42 which is encapsulated by fluid contacting surfaces 41b and 43b and a thin-walled sleeve 24 hereinbefore described. Lens 41 and 43 are attached to sleeve 24 by a fastening means to form a liquid-tight seal.

The configuration of triplet 40 is defined by object plane 39, a field lens 41, a concavo-convex liquid lens 42, correcting lens 43 and plane 45. An aperture stop is provided at plane 45 to define the aperture of the assembly. A field stop is also provided at plane 39 to define the diametral extent of the field of the assembly. As in the case of the Embodiment 8, the correcting lenses 41 and 43 are constructed of polystyrene and the optical liquid in fluid lens 42 is sterile water.

The large difference in indices of refraction and v-value across surfaces 41b and 43b corrects the assembly for curvature of field and primary axial color. As in the case of the other preferred embodiments, the thickness of fluid lens 42 is used to adjust track length to a specified value, as well as positioning the entrance pupil an infinite distance from the exterior surface 41a of the assembly. The proper spacing of this module to its symmetrical pair (thus constituting an image transmitting optical system) and to adjacent image transmitting optical systems is conveniently provided by tubular spacers (Not shown in FIG. 9). Surface 42a is a conic section, an oblate spheroid, which corrects the assembly for spherical aberration.

Lenses 41 and 43 are preferably fabricated by a precision injection molding process. As in Embodiment 8, this configuration, which is simplistically composed of plastic and water, also affords a cost-effective approach to the serial production of rod-like lenses of image transmitting optical systems. The data for Embodiment 9 will now be given.

Embodiment 9

Figure 21:
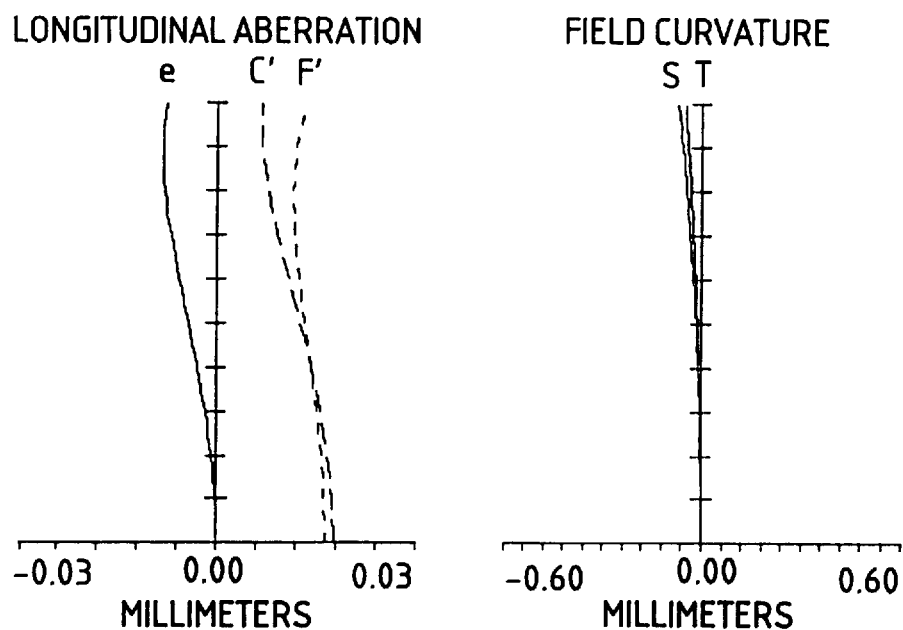

$NA_0$=0.0565 Object Distance=1.09 ½ Track=31.80
OBJECT
$T_{0,1}$=3.126 AIR
$R_1$=57.321
$T_{1,2}$=1.000 $N_{1,2}$=1.59501 $v_{1,2}$=30.62
$R_2$=−6.978
$T_{2,3}$=26.674 $N_{2,3}$=1.33447 $v_{2,3}$=56.00
$R_3$=−3.505
$T_{3,4}$=1.000 $N_{3,4}$=1.59501 $v_{3,4}$=30.62
$R_4$=−5.534 $k_4$=0.1793639
$T_{4,5}$=0.100 AIR
APERTURE STOP The aberration characteristics of Embodiment 9 when arranged in symmetrical opposing pairs of modules about the aperture stop plane is shown in FIG. 21.

Having characterized the construction of biconvex rod-like lenses of the present invention in terms of the shape and power of their constituent fluid lenses, we have previously examined the biconvex (positive power), bi-concave (negative power), and concavo-convex (positive power) variations. Now, in the preferred Embodiments 10 and 11 of the present invention, we describe bi-convex rod-like lenses containing fluid lenses which are plano-plano in shape and which exhibit zero optical power.

Figure 11:
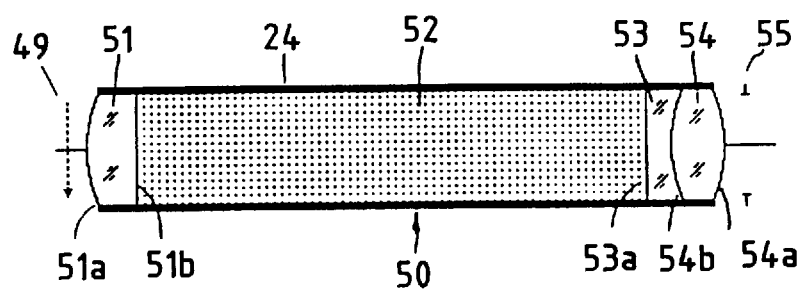
FIG. 11 is a sectional view of a rod lens according to Embodiments 10 of the present invention.
Figure 14:
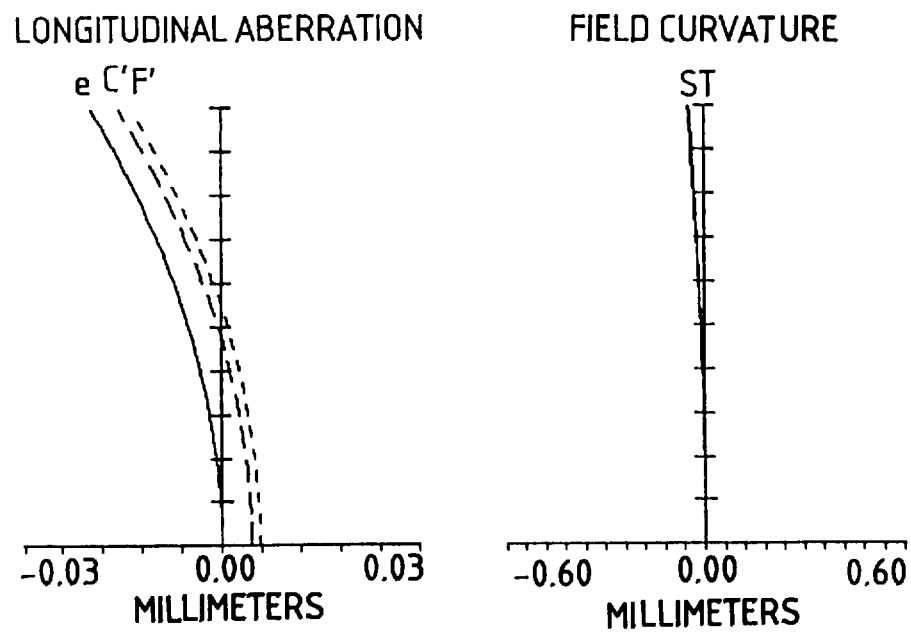
Figure 15:
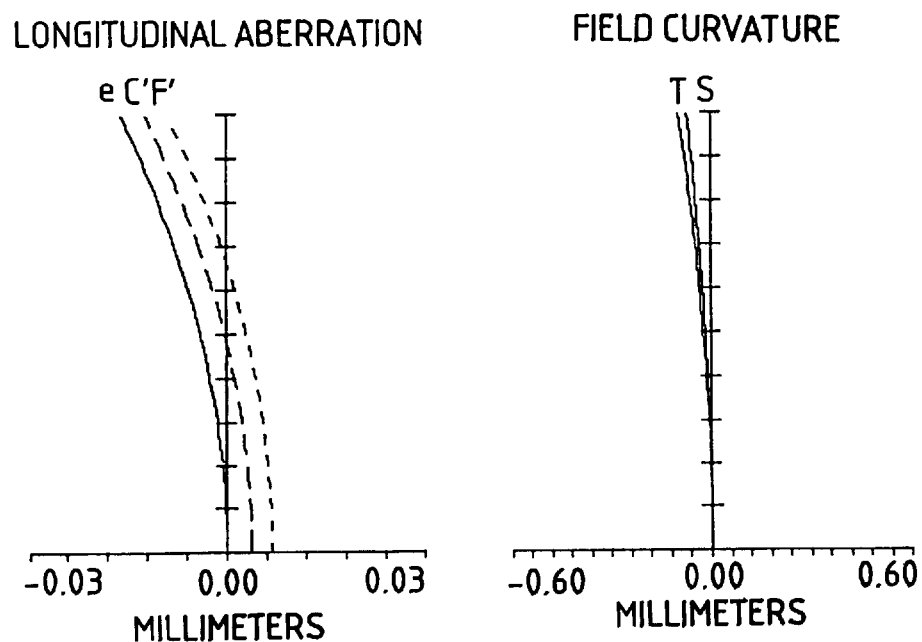
Figure 16:
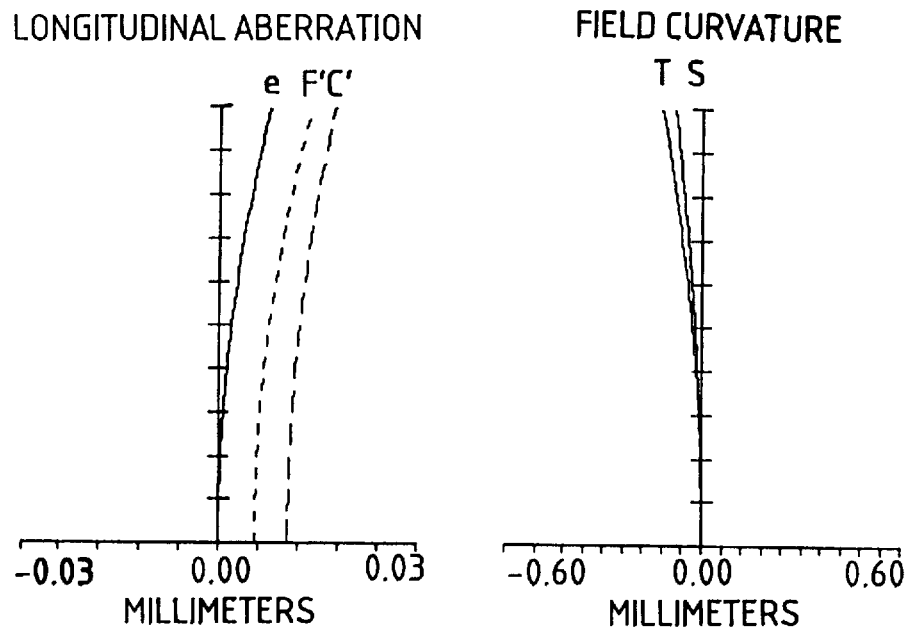
Figure 17:
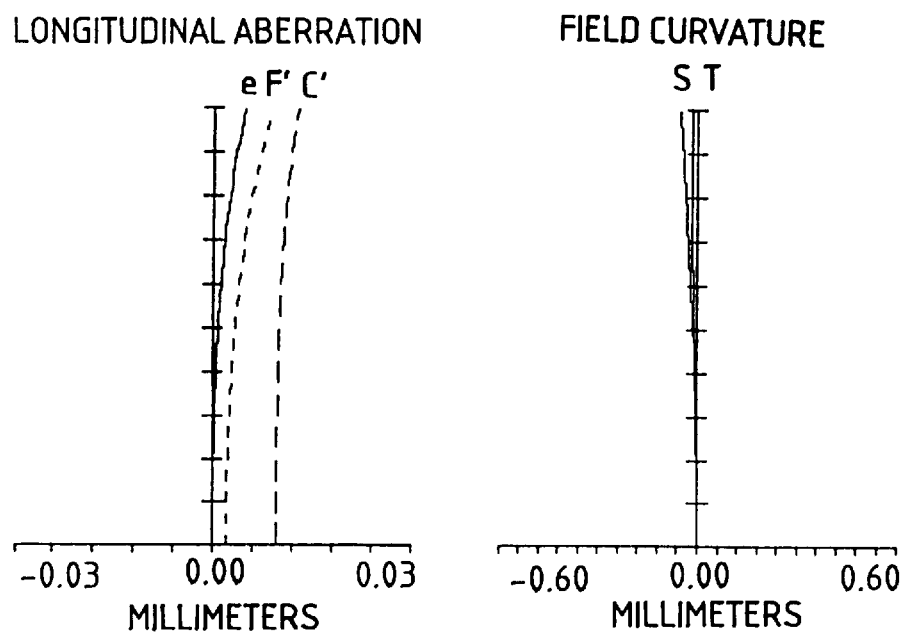
Figure 18:
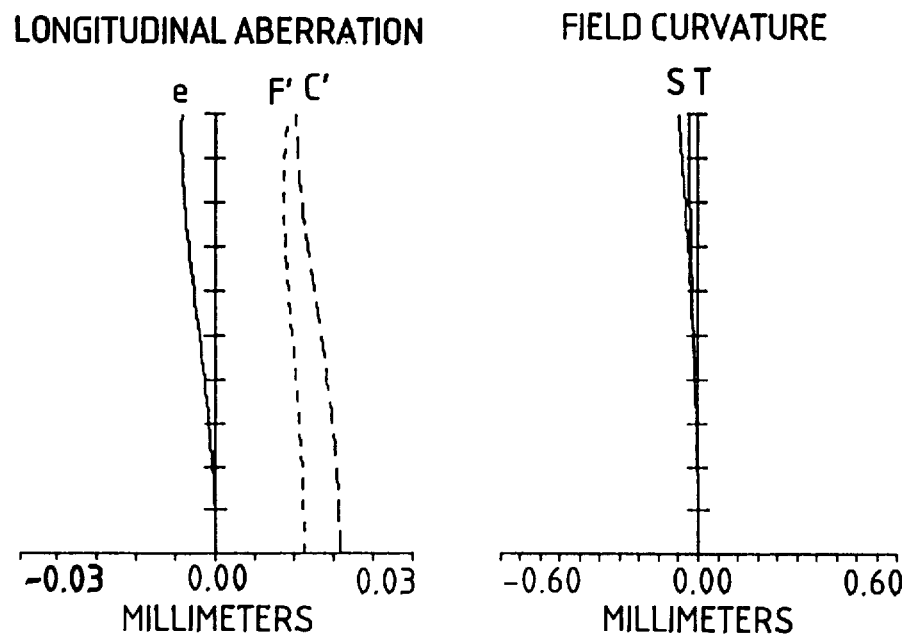
Figure 19:
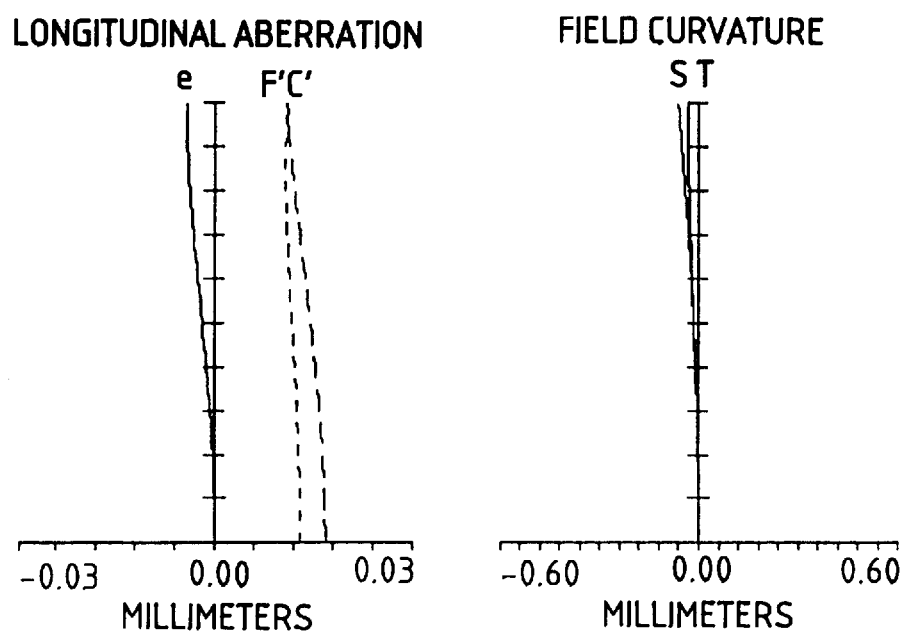
Figure 20:
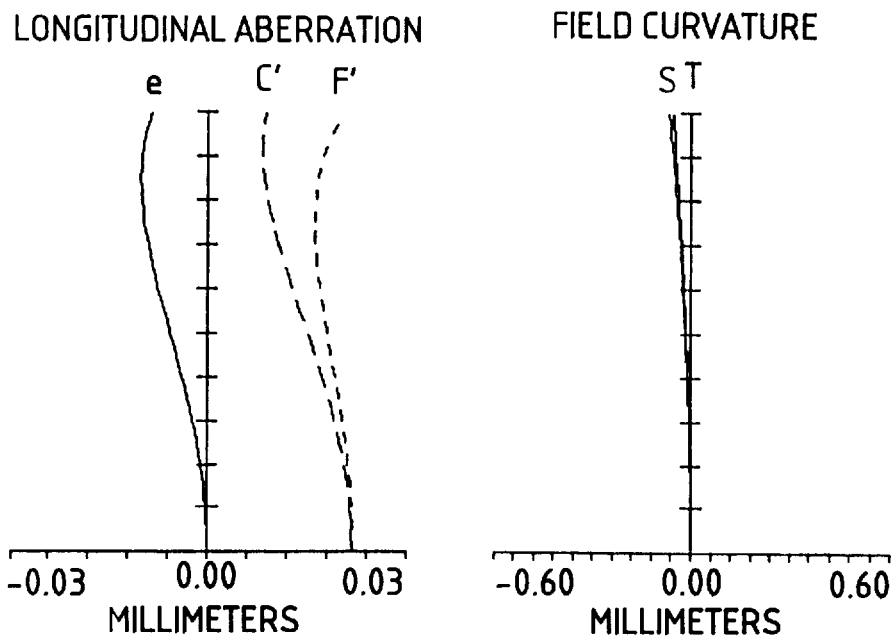

Embodiment 10 of the present invention, the diagrammatic axial section of which is shown in FIG. 11, is a module comprising an axially aligned quadruplet lens assembly 50. Quadruplet 50 includes field lens 51, a cemented achromatic doublet composed of lenses 53 and 54, said field lens and doublet separated by an optical fluid lens 52. Fluid lens 52 is encapsulated by fluid contacting surfaces 51b and 53a and a thin-walled sleeve 24 hereinbefore described. Lens elements 51, 53, and 54 are attached to sleeve 24 by a fastening means to form a liquid-tight seal. The configuration of the quadruplet 50 is defined by object plane 49, a field lens 51, a plano-plano liquid lens 52, a cemented achromatic doublet (lenses 53 and 54) and a pupil plane 55.

An aperture stop is provided at surface 55 to define the aperture of the assembly 50. A field stop is similarly provided at surface 49 to define the diametral extent of the field. The proper spacing of this module to its symmetrical counterpart and to adjacent image transmitting system is conveniently provided by tubular spacers (not shown in FIG. 11).

Whereas the flexible fluid middle portion 52 of the half module 50 of an image transmitting system is a cylindrically shaped element having no optical power, the assemblage derives its focal length (1/power) from the cemented doublet being composed of a light lanthanum crown (LaK) glass element 54 bonded to a dense barium flint glass (BaF) element 53. A field lens 51 is made of a dense flint (SF) glass. The fluid middle portion 52 of the assembly is a non-toxic, non-viscous, low index, "crown-like" optical liquid.

The index and v-value differences across surface 54b provides correction of curvature of field and primary axial color to acceptable residuals. Field lens 51 provides for telecentricity in both the object and image spaces. The center thickness of plano-plano fluid lens 52 provides for the required track length of the assembly.

Embodiment 11 of the present invention, the diagrammatic axial section of which is shown in FIG. 12, is an axially aligned quintuplet lens assembly 60. Quintuplet 60 consists of two similarly constructed achromatic doublets 61 and 61', composed respectively of bi-convex lenses 61 and 61' and plano-concave lenses 63 and 63', arranged in a front-to-back symmetry manner and separated by an optical fluid 62, which is encapsulated by fluid contacting surfaces 63b and 63b' and a thin-walled sleeve 24. The two cemented achromats are fastened to sleeve 24, as described above, to form a liquid-tight seal.

The configuration of quintuplet 60 is defined by object plane 59, two cemented doublets (lens elements 61, 63, and 61' and 63'), and pupil plane 65. A field stop and aperture stop is provided at object plane 59 and pupil plane 65, to respectively define the extent of the field and aperture of the assemblage. The proper spacing of quintuplet 60 to its symmetrical counterpart and adjacent image transmitting optical systems is provided by tubular spacers (not shown in FIG. 12).

The refractive materials utilized in half-module quintuplet 60 of the image transmitting optical system consists of two similarly constructed achromatic doublets made of a light lanthanum crown (LaK) glass in lens 61 and 61', and a dense barium flint (BaF) glass in lens 63 and 63', and a fluid middle portion 62 of a non-toxic, non-viscous, "crown-like" optical liquid.

Spherical aberration and primary axial color are favorably corrected by bending the surfaces of the achromat adjacent to the aperture stop 65. Curvature of field and astigmatism are favorably corrected by bending the surfaces of the achromat adjacent to the field stop surface 59. The center thickness of the plano-plano fluid lens 62 provides for the correction of the required track length and pupil telecentricity.

Although lens assemblies 50 and 60 are somewhat more complicated than that of the other 9 embodiments, the flexible middle portions 52 and 62 of the said assemblies reduces the likelihood of stress fracture occurring when the endoscope shaft is bent. Further, the material costs, the costs of fabrication, particularly when the achromatic doublets are identical in construction, and assembly are materially reduced over the all-glass counterparts of the prior art.

Now, the numerical data for Embodiments 10 and 11 of the present invention will be given. As in all cases above, the same nomenclature is utilized.

Figure 22:
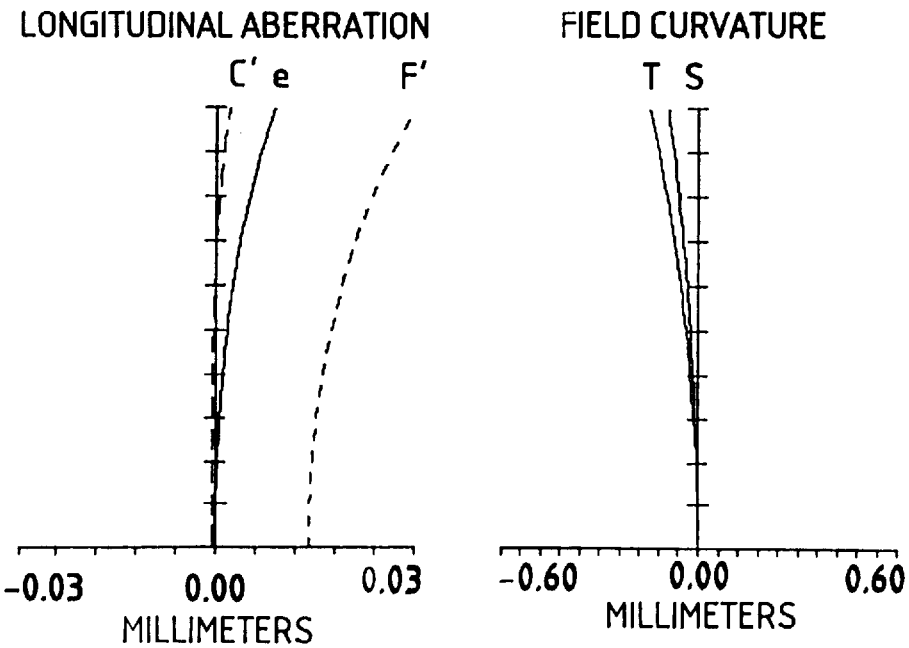
Figure 23:
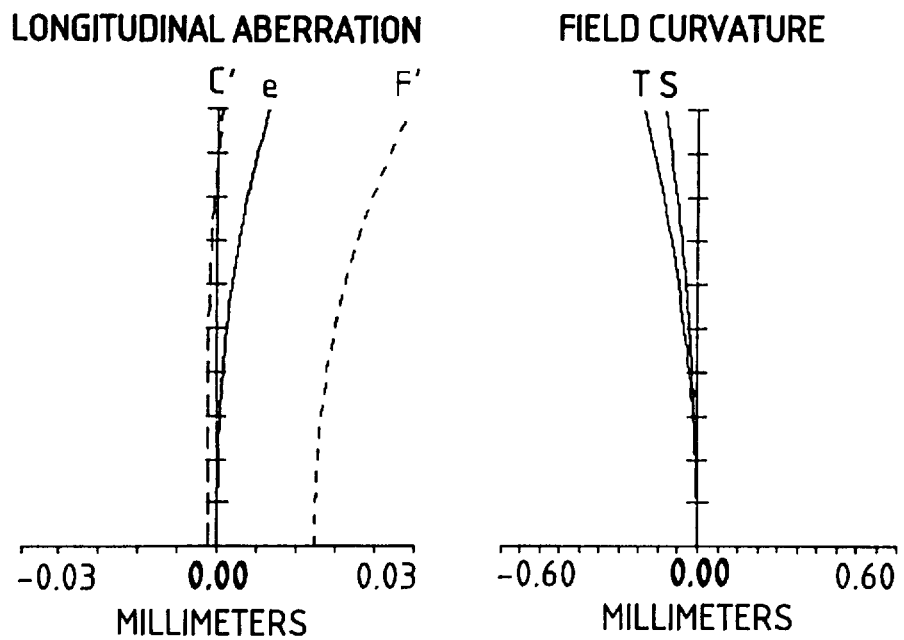

Embodiment 10
$NA_0$=0.0625 Object Diameter=2.12 ½ Track=31.80
OBJECT
$T_{0,1}$=1.211 AIR
$R_1$=14.050
$T_{1,2}$=1.000 $N_{1,2}$=1.65222 $v_{1,2}$=33.61
$R_2$=PLANO
$T_{2,3}$=27.617 $N_{2,3}$=1.40939 $v_{2,3}$=68.39
$R_3$=PLANO
$T_{3,4}$=1.000 $N_{3,4}$=1.65569 $v_{3,4}$=38.40
$R_4$=5.090
$T_{4,5}$=0.922 $N_{4,5}$=1.64514 $v_{4,5}$=57.72
$R_5$=−13.987
$T_{5,6}$=0.050 AIR
APERTURE STOP Embodiment 11
$NA_0$=0.060 Object Diameter=2.20 ½ Track=31.80
OBJECT
$T_{0,1}$=1.524 AIR
$R_1$=13.984
$T_{1,2}$=1.000 $N_{1,2}$=1.64514 $v_{1,2}$=57.70
$R_2$=−5.048
$T_{2,3}$=0.895 $N_{2,3}$=1.65569 $v_{2,3}$=44.64
$R_3$=PLANO
$T_{3,4}$=26.387 $N_{3,4}$=1.40939 $v_{3,4}$=68.39
$R_4$=PLANO
$T_{4,5}$=0.895 $N_{4,5}$=1.65569 $v_{4,5}$=44.64
$R_5$=5.048
$T_{5,6}$=1.000 $N_{5,6}$=1.64514 $v_{5,6}$=57.70
$R_6$=−13.984
$T_{6,7}$=0.100 AIR
APERTURE STOP The aberration characteristics of Embodiment 10 when arranged in a symmetrical opposing pair of modules about a common aperture stop plane is shown in FIG. 22. Similarly, the aberration characteristics of Embodiment 11 (when paired with its inverted common module) is shown in FIG. 23.

Figure 1:
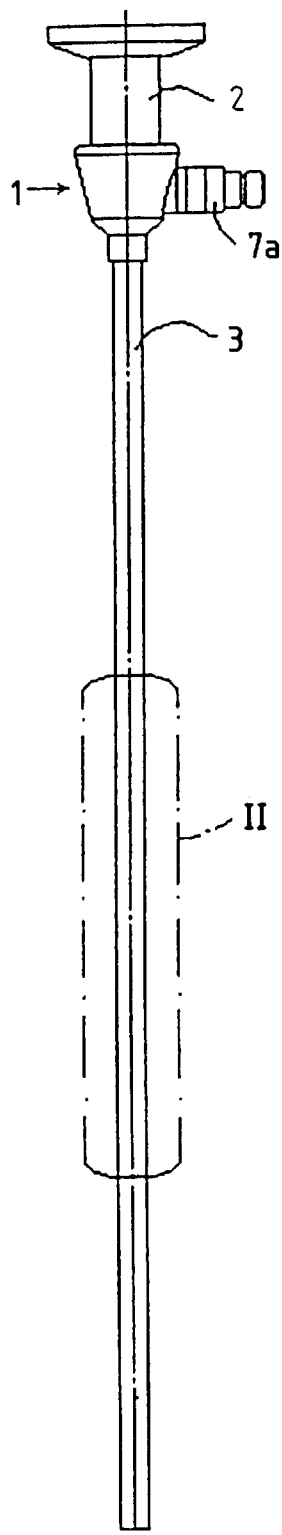
FIG. 1 is a side view of an inflexible type endoscope optics assembly.
Figure 1A:
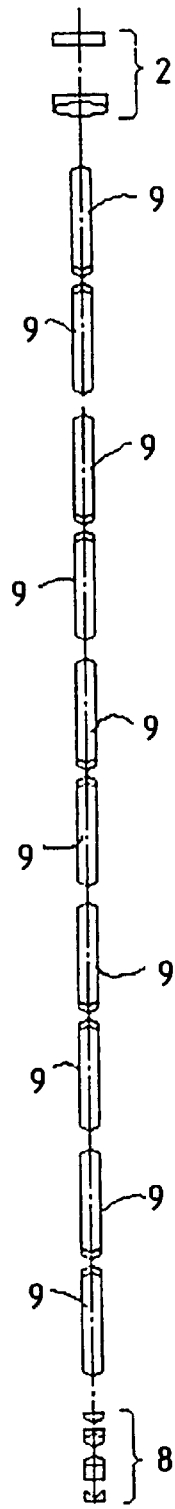
FIG. 1A is an optical schematic of the optical system contained within the shaft of the endoscope optics assembly.
Figure 24:
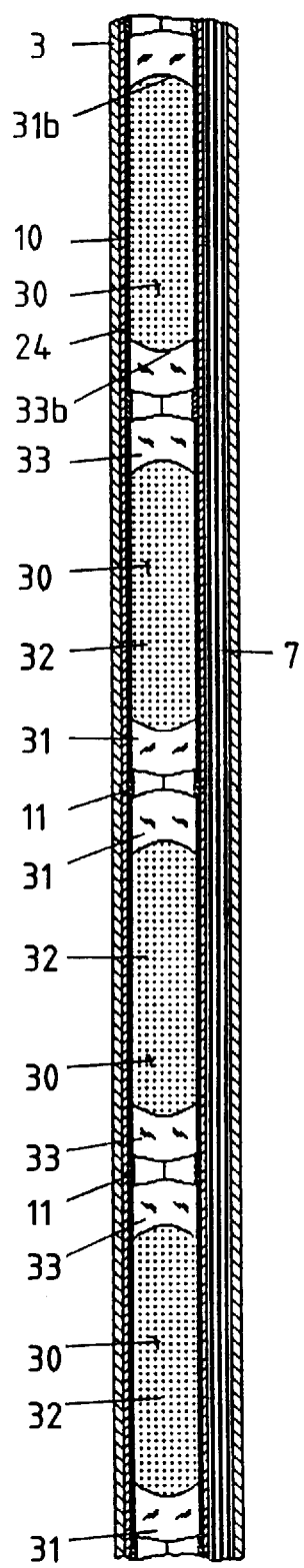
FIG. 24 is a diagrammatic axial section view through part of the distal portion of the endoscope assembly, and of the image transmitting optical system according to preferred Embodiment 8 of the present invention.

FIG. 24 illustrates a cross sectional view of the preferred Embodiment 8 of the present invention arranged as two in-tandem image transmitting optical systems within the distal section of the shaft 3 of an inflexible type endoscope 1 (see FIG. 1). Two pairs of modules, defining an image transmitting optical system, are illustrated wherein each module is identically composed of two rod-like fluid encapsulated assemblies 30 disposed in front-to-back symmetry about their respective aperture stop plane 35 (not shown). Each image transmitting optical system is then positioned so that the image plane of one is juxtaposed with the object plane 29 (not shown) of the ensuing image transmitting optical system.

The said assemblies are embraced in a thin-walled inner tube 10 within the outer shaft 3. The said rod-like fluid encapsulated assemblies 30 are supported by a thin-walled tube 24 within inner tube 10. Tube 24 and inner tube 10 cooperate in a close tolerance diametral fit in such manner that the prescribed volume of liquid 32 encapsulated within sleeve 24 and between liquid contacting surfaces 31b and 33b form a cylindrical cross section whose outer diameter corresponds to the inner diameter of inner tube 10. Lens 31 and 33 are longitudinally positioned at their proper separation (e.g., $T_{2,3}$ given in the numerical data for Embodiment 8) due to the incompressibility of property of the liquid. The rod-like fluid encapsulated assemblies are held in longitudinally spaced relationship to one another by means of thin-walled tubular spacers 11.

In summary, it can be seen that the present invention, in which 11 different configurations of rod-like fluid encapsulated rod-like lens have been presented, provides a lens module which eliminates the need for multiple glass element cemented assemblies in image transmitting optical systems. In most embodiments the rod-like lens simply consist of two lens elements and a fluid therebetween.

The features of the present invention include:
1. Insensitivity to glass fracture or breakage when shear and compressive forces are applied;
2. Economy in manufacture and assembly; and
3. Residual values of composite image errors which are generally less than other prior art image transmitting optical systems.

While the above description contains many specificities, these should not be construed as limitations on the scope of the invention, but rather as exemplifications of the preferred embodiments thereof. Many other variations are possible, for example, the means of encapsulation, the use of aspheric surfaces other than conic constants, the choice of refractive materials, etc. Accordingly, the scope of the invention should be determined not by the embodiments illustrated, but by the appended claims, or their equivalents.

What is claimed is:

1. A biconvex rod lens for an image transmission optical system, the rod lens comprising a sleeve containing at each of its end portions a correcting lens, said correcting lenses and said sleeve defining an enclosed space and encapsulating a light transmitting fluid, which is a liquid filling and constituting essentially the sole contents of the enclosed space.

2. A biconvex rod lens for an image transmission optical system, the rod lens comprising a sleeve containing at each of its end portions a correcting lens, said correcting lenses and said sleeve encapsulating a light transmitting fluid exhibiting optical properties of flint glass.

3. A rod lens as claimed in claim 2 wherein the correcting lenses at each end portion of the sleeve have positive optical power and are biconvex in shape.

4. A rod lens as claimed in claim 3 wherein the correcting lenses at each end portion of the sleeve are made of polymethyl methacrylate.

5. A biconvex rod lens for an image transmission optical system, the rod lens comprising a sleeve containing at each of its end portions a correcting lens, said correcting lenses and said sleeve encapsulating a non-aqueous, light transmitting fluid exhibiting optical properties of crown glass.

6. A rod lens as claimed in claim 5 wherein the correcting lenses at each end portion of the sleeve have negative optical power and are convex-concavo in shape.

7. A rod lens as claimed in claim 6 wherein the correcting lenses at each end portion of the sleeve are made of polystyrene (styrene).

8. A rod lens as claimed in claim 7 wherein the encapsulated fluid is sterile water.

9. A rod lens as claimed in claim 5 wherein the correcting lens at one end portion of the sleeve has positive optical power and is biconvex in shape, whereas the correcting lens at the opposite end portion of the said sleeve is of negative optical power and is concavo-convex in shape.

10. The rod lens as claimed in claim 9 wherein the connecting lenses at each end portion of the sleeve are made of polystyrene.

11. A rod lens as claimed in claim 10 wherein the encapsulated fluid is sterile water.

12. A biconvex rod lens for an image transmission optical system, the rod lens comprising a sleeve containing at each of its end portions a correcting lens, said correcting lenses and said sleeve encapsulating a non-aqueous, light transmitting fluid wherein the correcting lens at one end of the sleeve has positive optical power and is plano-convex in shape, whereas the correcting lens at the opposite end of the sleeve is a cemented achromatic doublet having positive optical power, said doublet including a biconvex lens, made of a material having optical properties of crown glass, and a plano-convex lens made of a material having optical properties of flint glass.

13. A rod lens as claimed in claim 12 wherein the encapsulated fluid is a liquid having optical properties of crown glass.

14. A biconvex rod lens for an image transmission optical system, the rod lens comprising a sleeve containing at each of its end portions a correcting lens, said correcting lenses and said sleeve encapsulating a non-aqueous, light transmitting fluid wherein the correcting lenses at the end portions of the sleeve are a cemented achromatic doublets having positive optical power, each said doublet including a biconvex lens, made of a material having optical properties of crown glass, and a plano-convex lens made of a material having optical properties of flint glass.

15. A rod lens as claimed in claim 14 wherein the encapsulated fluid is a liquid having optical properties of crown glass.

16. A rod lens as claimed in claim 1 wherein the encapsulated fluid exhibits optical properties of flint glass.

17. A rod lens as claimed in claim 1 wherein the encapsulated fluid exhibits optical properties of crown glass.

18. A biconvex rod lens for an image transmission optical system, the rod lens comprising a sleeve containing at each of its end portions a correcting lens, said correcting lenses and said sleeve defining an enclosed space and encapsulating a transmitting fluid, wherein at least one of said correcting lenses is non-concave where contacted by the light transmitting fluid.

19. A rod lens as claimed in claim 18 wherein at least one of said correcting lenses is convex where contacted by the light transmitting fluid.

20. A rod lens as claimed in claim 18 wherein at least one of said correcting lenses is planar where contacted by the light transmitting fluid.

21. A rod lens as claimed in claim 19 wherein both of said correcting lenses are convex where contacted by the light transmitting fluid.

22. A rod lens as claimed in claim 20 wherein both of said correcting lenses are planar where contacted by the light transmitting fluid.

23. A rod lens as claimed in any one of claims 1 through 22 wherein the encapsulated fluid is water.

24. A rod lens as claimed in any one of claims 1 through 22 wherein the encapsulated fluid is non-aqueous, non-toxic, and non-viscous.

* * * * *